(12) United States Patent
Bonelli et al.

(10) Patent No.: US 12,186,168 B2
(45) Date of Patent: Jan. 7, 2025

(54) APPARATUS FOR PRODUCING SANITARY ABSORBENT ARTICLES COMPRISING A PERFORATING DEVICE OF A WEB AND PROCESS

(71) Applicant: Fameccanica.Data S.p.A., San Giovanni Teatino (IT)

(72) Inventors: Guido Bonelli, Pescara (IT); Paolo Gagliardone, Alanno (IT)

(73) Assignee: Fameccanica.Data S.p.A., San Giovanni Teatino CH (IT)

( * ) Notice: Subject to any disclaimer, the term of this patent is extended or adjusted under 35 U.S.C. 154(b) by 1422 days.

(21) Appl. No.: 16/714,860

(22) Filed: Dec. 16, 2019

(65) Prior Publication Data

US 2020/0206038 A1 Jul. 2, 2020

(30) Foreign Application Priority Data

Dec. 27, 2018 (IT) .................. 102018000020542

(51) Int. Cl.
*A61F 13/512* (2006.01)
*A61F 13/15* (2006.01)
*A61F 13/513* (2006.01)

(52) U.S. Cl.
CPC ...... *A61F 13/15731* (2013.01); *A61F 13/512* (2013.01); *A61F 13/51394* (2013.01); *A61F 2013/15934* (2013.01)

(58) Field of Classification Search
CPC .............. A61F 13/15731; A61F 13/512; A61F 13/51394; A61F 2013/15934; A61F 13/15707; B26F 1/10
See application file for complete search history.

(56) References Cited

U.S. PATENT DOCUMENTS

| | | | | |
|---|---|---|---|---|
| 8,287,977 B2 * | 10/2012 | McNeil | .................. | D21H 27/02 162/114 |
| 8,502,013 B2 * | 8/2013 | Zhao | ....................... | A61F 13/47 604/385.101 |
| 8,535,483 B2 * | 9/2013 | McNeil | ................. | D21F 11/008 162/362 |
| 9,028,652 B2 * | 5/2015 | Curro | ....................... | B31F 1/07 162/204 |
| 9,358,705 B2 * | 6/2016 | Zhao | ....................... | B29C 65/02 |
| 9,849,602 B2 * | 12/2017 | Cree | .................... | A61F 13/5121 |
| 9,918,596 B2 * | 3/2018 | Olson | .................... | D21H 27/002 |
| 10,524,622 B2 * | 1/2020 | Olson | .................... | D21H 27/002 |
| 10,766,186 B2 * | 9/2020 | Zhao | ....................... | B29C 65/02 |

(Continued)

FOREIGN PATENT DOCUMENTS

| | | | | |
|---|---|---|---|---|
| CA | 2743692 C | * | 3/2018 | ............ A47K 10/16 |
| ES | 2891009 T3 | * | 1/2022 | ....... A61F 13/15707 |
| WO | 2016073694 A1 | | 5/2016 | |

OTHER PUBLICATIONS

Italian Search Report dated Jul. 4, 2019. 7 pages.

*Primary Examiner* — Jose A Fortuna
(74) *Attorney, Agent, or Firm* — RMCK Law Group PLC

(57) ABSTRACT

An apparatus for producing sanitary absorbent articles comprising at least one perforating device of at least one web intended for making sanitary absorbent articles capable of making perforated patterns spaced apart along the extension of the web, that is, in phase. The present invention also relates to a perforating process implemented in an apparatus for producing sanitary absorbent articles.

17 Claims, 2 Drawing Sheets

(56) References Cited

U.S. PATENT DOCUMENTS

| | | | |
|---|---|---|---|
| 11,364,156 B2* | 6/2022 | Zhao | A61F 13/533 |
| 11,707,162 B2* | 7/2023 | Olson | C09D 5/00 |
| | | | 162/117 |
| 2008/0221539 A1* | 9/2008 | Zhao | A61F 13/535 |
| | | | 604/378 |
| 2010/0036346 A1 | 2/2010 | Hammons et al. | |
| 2012/0273148 A1* | 11/2012 | Orr | D21H 27/002 |
| | | | 162/204 |
| 2012/0276238 A1 | 11/2012 | Strube et al. | |
| 2013/0304012 A1* | 11/2013 | Zhao | A61F 13/15707 |
| | | | 604/374 |
| 2015/0173970 A1 | 6/2015 | Gross et al. | |
| 2015/0230993 A1* | 8/2015 | Curro | D21F 11/006 |
| | | | 264/175 |
| 2016/0338879 A1* | 11/2016 | Zhao | A61F 13/533 |
| 2017/0037579 A1* | 2/2017 | Marietta-Tondin | D21H 27/005 |
| 2020/0206038 A1* | 7/2020 | Bonelli | A61F 13/15731 |
| 2023/0007888 A1* | 1/2023 | Sablone | A61F 13/15699 |
| 2024/0000273 A1* | 1/2024 | Olson | C09D 5/00 |

\* cited by examiner

APPARATUS FOR PRODUCING SANITARY ABSORBENT ARTICLES COMPRISING A PERFORATING DEVICE OF A WEB AND PROCESS

CROSS-REFERENCE TO RELATED APPLICATION

This application claims priority to Italian Patent Application No. 102018000020542 filed Dec. 27, 2018. The disclosure of the above application is incorporated herein by reference in its entirety.

TECHNICAL FIELD

Embodiments of the present invention relate to an apparatus for producing sanitary absorbent articles comprising at least one perforating device of at least one web intended for making sanitary absorbent articles, such as diapers, diaper-pants, incontinence pads, sanitary pads, or other articles intended to absorb bodily fluids.

Embodiments of the present invention relate to a perforating device usable in an apparatus for producing sanitary absorbent articles having portions provided with one or more perforated patterns in relation to the desired production requirements.

Here and hereinafter perforated pattern of a web and/or of a portion of sanitary absorbent article means a spatially delimited zone wherein holes spaced apart are present.

The present invention also relates to a perforating process implemented in an apparatus for producing sanitary absorbent articles comprising at least one perforating device capable of making perforated patterns on at least one web intended for making sanitary absorbent articles.

BACKGROUND ART

There are known sanitary absorbent articles provided with one or more perforated patterns, which give particular properties to the zones where they are made.

In relation to the specific zone where such perforated patterns are made, to the particular shape and/or to the arrangement of the holes by which they are constituted, it is possible to locally increase various properties of the sanitary absorbent article, such as the breathability, the capacity for absorption, the softness to the touch, the flexibility along various directions, or other.

To obtain sanitary absorbent articles having one or more perforated patterns without imperfections, or in any case rapidly, it is known that the webs are purchased already perforated and are cut in line according to production requirements.

That known solution involves high costs, requires lengthy times for loading in line and for supplying, and necessitates large warehouse spaces and numbers of personnel.

It is known that the use of webs already perforated is also disadvantageous from an operating viewpoint, since the relative mechanical properties are notably different from those of a non-perforated web.

That requires dedicated designs of the production apparatus for each type of already perforated web which, as well as notably complicating the production line processing steps, are not very suitable for other types of web.

In this context, if the intention is to change an already perforated web with another web of another type, it is necessary to reconfigure most of the processing units by which the production apparatus is constituted.

Due to the intrinsic deterioration of the already perforated webs over time, the properties of the latter may change up to the point that they are no longer suitable for producing sanitary absorbent articles.

That involves considerable economic losses, aggravated by the burden of having to dispose of the webs which have deteriorated and are no longer usable.

In other technological sectors, it is known that webs are made having a plurality of continuous holes constituting a single perforated pattern which extends for the whole length of the web.

Such solutions provide for the use of a calendar provided with one or more pairs of rollers on which a plurality of needles, or protruding elements are present, suitable for perforating the web while it passes through the calendar itself.

However, such known solutions cannot be used effectively in the sector for making sanitary absorbent articles, since they do not allow the rapid and in line making of perforated patterns which are spatially delimited and spaced apart along the extension of the web.

Here and hereinafter extension of the web means the extension of the web in the sense of its length, that is to say, along the machine direction if the web is advanced with its longitudinal axis along the machine direction.

Using such known solutions it is not possible to make webs having perforated patterns spaced apart along the extension of the web and on which different processing can be performed in line such as printing, welding, embossing, cutting, or other.

Other known solutions provide for the use of perforating devices installed in line which, as well as being bulky, do not allow the obtainment of holes which are uniform, without imperfections and require the web to be temporarily stopped, or notably slowed.

That involves a notable overall slowing in the production of the sanitary absorbent articles no longer acceptable due to the technical and commercial requirements of the sector.

Moreover, the holes made in the web with the known solutions may have unwanted elliptical shapes and/or lacerated and/or stretched portions, or in the worst cases the web may even remain accidentally caught in the perforating device.

Therefore, the need exists to improve and make available a perforating device, a production apparatus comprising that perforating device, as well as a perforating process which overcome at least one of the disadvantages of the prior art.

One aim of the present invention is to supply an apparatus for producing sanitary absorbent articles comprising a perforating device capable of making perforated patterns spaced apart along the extension of the web directly in line and with high production rates.

A further aim of the present invention is to supply an apparatus for producing sanitary absorbent articles comprising a perforating device capable of making in line perforated patterns in a web which are precise and without imperfections so as to obtain sanitary absorbent articles corresponding to design expectations.

It is also an aim of the present invention to supply an apparatus for producing sanitary absorbent articles comprising a perforating device capable of guaranteeing high performance and stability, that is to say, such that it does not require frequent interventions by operators.

It is a further aim of the present invention to supply an apparatus for producing sanitary absorbent articles capable of making at least one web comprising perforated patterns in phase, that is to say, spaced apart, and in correspondence with which it is possible to effectively perform more and different processing.

It is also an aim of the present invention to supply a perforating process implemented in an apparatus for producing sanitary absorbent articles comprising a perforating device which allows the rapid and controlled making of perforated patterns spaced apart along the extension of the web in line, that is to say, in phase.

To overcome the disadvantages of the prior art and to obtain these and further aims and advantages, the Applicant has devised, tested and made the present invention.

DISCLOSURE OF THE INVENTION

The present invention is expressed and characterized in the independent claims, while the dependent claims explain other characteristics of the present invention or variants of the main solution idea.

In accordance with the above-mentioned aims, possible embodiments of the present invention relate to an apparatus for producing sanitary absorbent articles comprising at least one perforating device of at least one web intended for making sanitary absorbent articles.

According to possible embodiments, the perforating device comprises a first roller and a second roller respectively provided with a first mantle and a second mantle and between which, in use, the web passes.

In accordance with possible embodiments, the first roller and the second roller are configured to rotate in opposite directions respectively around a first axis of rotation at a first velocity and around a second axis of rotation, parallel to the first axis of rotation, at a second velocity different from the first velocity.

According to possible embodiments, the first mantle comprises a first protruding pattern and the second mantle comprises at least a first zone, wherein a second protruding pattern is present, and at least a second zone without protruding patterns.

In accordance with possible embodiments, the second zone is adjacent to the first zone along a circumference of the second mantle.

According to possible embodiments, the second protruding pattern is configured, in use, to temporally engage the web with the first protruding pattern without interpenetrating the latter for locally perforating the web.

The perforating device allows the obtainment of perforated patterns spaced apart along the extension of the web directly in line and rapidly while the web passes through the pair of rollers.

Following the localized engagement between the protruding patterns and the difference of velocity between the two rollers, the web is locally perforated in correspondence with the engagement zones of the protruding patterns with the web.

Thanks to the sequential and intermittent engagement of the first protruding pattern and of the second protruding pattern with the web without the two protruding patterns interpenetrating each other, that is to say, meshing with each other, it is possible to make a plurality of holes constituting perforated patterns spaced apart.

Following the engagement of the protruding patterns at different velocity, the fibres of the web are spaced apart and/or locally removed to form the holes of which the perforated patterns are composed.

The joint action of the protruding patterns also allows the fibres of the web to be fixed in correspondence with the edge of the holes so that they keep the shape even after the disengagement of the protruding patterns.

The possibility of using such rollers directly in line renders the production apparatuses capable of making sanitary absorbent articles provided with perforated patterns with high production rates, simultaneously guaranteeing high stability in the processes.

The perforating device allows the web to be perforated intermittently, that is to say, in phase, starting from a web without holes, while it passes through the pair of rollers.

One of the advantages of feeding the production apparatus with a non-perforated web and of perforating it in line notably reduces any need to redesign and/or substitute extensive portions of the production apparatus as happens in the prior art when another type of already perforated web is used.

The perforating device therefore allows the use of different webs and making of the holes when necessary along the advancement path of the web in the apparatus so as to be able to design portions of the apparatus in a unique way for performing processing on non-perforated webs which may even be different from each other.

The mechanical properties of the non-perforated webs allow simplification of the processing units of the production apparatus and therefore keeping the designs dedicated to perforated webs only in the portions of the apparatus downstream of the perforating device.

That allows the design and making of production apparatuses which are less complex and have fewer processing units, thereby also reducing the dimensions of the overall apparatus.

The combination of a first mantle having a first protruding pattern with a second mantle having portions with a second protruding pattern and zones without protruding patterns guarantees a high stability of the intermittent perforating process since engagement of the protruding patterns with each other is guaranteed.

Thanks to the presence on the second roller of first and second zones adjacent along a circumference of the second mantle it is possible to make in sequence perforated patterns spaced apart along the extension of the web.

In accordance with possible embodiments, the second mantle may comprise a plurality of first zones and a plurality of second zones arranged alternately along a circumference of the second mantle.

According to possible embodiments, the first protruding pattern may have a protruding profile inclined by an angle of inclination with respect to the first axis of rotation equal to or less than 90°.

In accordance with possible embodiments, the second protruding pattern may have a protruding profile inclined by an angle of inclination with respect to the second axis of rotation equal to or less than 90°.

According to possible embodiments, the first protruding pattern and the second protruding pattern may have the same protruding profile inclined so that, in use, the respective inclined protruding profiles of the first protruding pattern and of the second protruding pattern intersect each other in localized zones of the web to locally perforate it.

In accordance with possible embodiments, the maximum distance between the second axis of rotation and the second zone may be less than the maximum distance between the second axis of rotation and the first zone.

According to possible embodiments, the perforating device may comprise at least one spacer member coupled with the first roller and/or with the second roller and configured, in use, to keep the first protruding pattern spaced apart from the surface of the second zone of the second mantle by a distance equal to the distance between the surface of the second zone of the second mantle and the outermost end of the second protruding pattern.

In accordance with possible embodiments, the perimeter of the first zone may be shaped in relation to the perimeter of the perforated pattern to be made on the web.

In accordance with possible embodiments, the production apparatus may comprise a printing unit placed upstream of the perforating device and configured to print a plurality of graphic patterns spaced apart along the extension of the web.

According to possible embodiments, the perforating device is configured to make holes in correspondence with the graphic patterns so as to make a plurality of perforated graphic patterns spaced apart along the extension of the web.

In accordance with possible embodiments, the first roller and/or the second roller are coupled with heating means configured to heat the first roller and/or the second roller for perforating, in use, the web heating it locally.

In accordance with possible embodiments, the present invention also relates to a process for perforating at least one web intended for making sanitary absorbent articles implemented in an apparatus for producing sanitary absorbent articles comprising at least one perforating device as in any of the embodiments of the present invention.

According to possible embodiments, the perforating process may provide to:
  supply the web along an advancement direction at an advancing velocity;
  pass the web between a first roller and a second roller respectively provided with a first mantle and a second mantle, wherein the first roller and the second roller rotate in opposite directions respectively around a first axis of rotation at a first velocity and around a second axis of rotation, parallel to the first axis of rotation, at a second velocity different from the first velocity, wherein the first mantle comprises a first protruding pattern and the second mantle comprises at least a first zone, wherein a second protruding pattern is present, and at least a second zone without protruding patterns and adjacent to the first zone along a circumference of the second mantle;
  perforating the web in correspondence with the engagement zones of the first protruding pattern and the second protruding pattern so as to make a plurality of perforated patterns spaced apart along the extension of the web.

In accordance with possible embodiments, the perforating process may provide that the advancing velocity is comprised between the first velocity and the second velocity.

According to possible embodiments, the perforating process may provide that the advancing velocity is equal to the first velocity or to the second velocity.

In accordance with possible embodiments, the perforating process may provide that the first protruding pattern and the second protruding pattern have a protruding profile inclined at the same angle of inclination with respect to the corresponding axis of rotation, wherein the process may provide to perforate the web in correspondence with the intersections of the inclined protruding profiles of the first protruding pattern and of the second protruding pattern.

According to possible embodiments, the perforating process may provide that the second zone does not touch the web while the latter passes between the first roller and the second roller.

In accordance with possible embodiments, the perforating process may provide to print a plurality of graphic patterns spaced apart on the web before making the perforated patterns.

According to possible embodiments, the perforating process may provide to make the perforated patterns in correspondence with the graphic patterns.

In accordance with possible embodiments, the perforating process may provide to make a plurality of embossing on the web after having made the perforated patterns.

According to possible embodiments, the perforating process may provide that the web is a composite web comprising a first layer of non-woven fabric, a second layer of non-woven fabric and at least one elastic element placed between the first layer and the second layer.

In accordance with possible embodiments, the perforating process may provide to locally weld the first layer and the second layer together while the elastic element is tensioned.

DESCRIPTION OF THE DRAWINGS

These and other characteristics of the present invention will be apparent from the following description of embodiments, supplied by way of example only, non-limiting, with reference to the appended drawings wherein.

For easier understanding, identical reference numbers have been used, where possible, to identify identical elements common to the figures. It shall be understood that elements and characteristics of one embodiment may be appropriately incorporated in other embodiments without further explanations.

DESCRIPTION OF EMBODIMENTS

Figure 1:
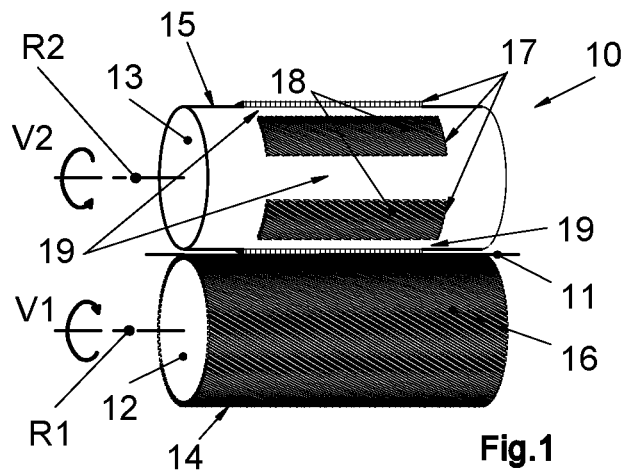
FIG. 1 schematically illustrates a perforating device of an apparatus for producing sanitary absorbent articles according to a possible embodiment of the present invention.
Figure 2:
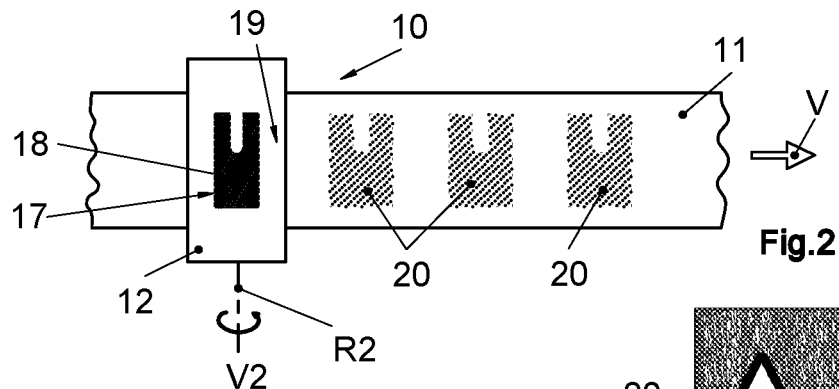
FIG. 2 schematically illustrates a perforating device of an apparatus for producing sanitary absorbent articles according to a possible embodiment of the present invention.

Embodiments described herein, with reference to the figures, relate to a perforating device 10 of at least one web 11 intended for making sanitary absorbent articles.

In accordance with possible embodiments, the perforating device 10 is configured to make perforated patterns 20 spaced apart along the extension of the web 11, wherein the perforated patterns 20 are provided with holes spaced apart.

For example, the web 11 may comprise a plurality of perforated patterns 20 having desired shapes and dimensions in relation to the perforating device 10 and to the operating parameters of the later.

According to possible embodiments, the perforating device 10 may comprise a first roller 12 and a second roller 13 respectively provided with a first mantle 14 and a second mantle 15 and between which, in use, the web 11 passes.

According to possible embodiments, the first roller 12 and the second roller 13 may be configured to rotate in opposite directions respectively around a first axis of rotation R1 at a first velocity V1 and around a second axis of rotation R2, parallel to the first axis of rotation R1, at a second velocity V2 different from the first velocity V1.

That allows the web 11 to be advanced through the two mantles 14 and 15 along a desired direction. Moreover, the different velocity of the two rollers 12 and 13 allows a plurality of localized holes to be made on the web 11.

In accordance with possible embodiments, the first roller 12 and the second roller 13 may rotate by means of a movement member. For example, the movement member may comprise a motor, an actuator and/or another movement system if necessary provided with means for the transmission and/or conversion of the motion.

According to possible embodiments, the rollers 12 and 13 may rotate in a coordinated way by means of a common movement member suitable for making both rollers rotate in a coordinated way.

In accordance with possible embodiments, the first mantle 14 may comprise a first protruding pattern 16.

According to possible embodiments, the first protruding pattern 16 may comprise a plurality of protrusions towards the outside of the first mantle 14.

For example, the first protruding pattern 16 may comprise a helical profile, that is to say, a continuous protrusion wrapped around the first roller 12 with a desired space between the coils.

According to possible embodiments, the helical profile may comprise a plurality of protrusions wrapped around the first roller 12 with a desired space between the coils.

In accordance with possible embodiments, the first mantle 14 may comprise at least one zone without protruding patterns adjacent to the first protruding pattern 16 along a circumference of the first mantle 14. The circumference may be defined as the perimeter of a section of the first mantle 14 orthogonal to the longitudinal axis of the first roller 12.

According to possible embodiments, between the zone without protruding patterns and the first protruding pattern 16, the latter may be connected to the surface of the first mantle 14.

That allows the avoidance of any snags and/or damage to the web 11 in correspondence with the passage of the latter on the edge of the first protruding pattern 16.

According to possible embodiments, the second mantle 15 may comprise at least a first zone 17, wherein a second protruding pattern 18 is present, and at least a second zone 19 without protruding patterns and adjacent to the first zone 17 along a circumference of the second mantle 15. The circumference may be defined as the perimeter of a section of the second mantle 15 orthogonal to the longitudinal axis of the second roller 13.

According to possible embodiments, the second protruding pattern 18 may comprise a plurality of protrusions towards the outside of the second mantle 15.

For example, the second protruding pattern 18 may comprise an inclined profile, that is to say, a plurality of protrusions placed on the second roller 13 with a desired space between them and delimited by the perimeter of the first zone 17.

According to possible embodiments, between the first zone 17 and the second zone 19, the second protruding pattern 18 may be connected to the surface of the second mantle 15.

In accordance with possible embodiments, the second protruding pattern 18 may be configured, in use, to temporally engage the web 11 with the first protruding pattern 16 without interpenetrating the latter for locally perforating the web 11.

In other words, the protrusions of the first protruding pattern 16 make contact with the protrusions of the second protruding pattern 18 without meshing with each other, that is to say, without the former positioning themselves between two consecutive protrusions of the latter.

According to possible embodiments, the web 11 is perforated following the contact and the relative movement of the first protruding pattern 16 with the second protruding pattern 18, that is to say, while the web 11 is placed between the protrusions of the first protruding pattern 16 and of the second protruding pattern 18 and the latter move with different velocities.

In this condition, the holes are made following the dragging at different velocities between the protrusions of the first protruding pattern 16 and of the second protruding pattern 18, that is to say, the fibres of which the web 11 is composed are locally shifted and/or are accumulated at the edges of the hole, that is to say, locally melted to each other, to form the holes.

According to possible embodiments, in relation to the relative velocities, or in any case in relation to the operating parameters of the rollers 12 and 13, it is possible to make the holes having perimetric profiles wherein the fibres are accumulated and if necessary associated with each other, for example welded, or heat-welded.

According to possible embodiments, one or both of the rollers 12 and 13 may be heated by means of suitable heating means coupled with them for performing the perforation by locally heating the web 11.

That improves the perforation performance and allows the perforation operation to be performed on webs 11 which may be deformed when their local temperature is greater than a threshold value.

According to possible embodiments, during the rotation the first protruding pattern 16 and the second protruding pattern 18 simultaneously and locally engage the web 11.

In accordance with possible embodiments, the perforating device 10 may be configured to apply a desired pressure while the first protruding pattern 16 and the second protruding pattern 18 simultaneously engage the web 11.

For example, it is possible to set and/or modulate the pressure between the two protruding patterns 16 and 18 by applying the desired force F to the axes of rotation of one or both of the rollers 12 and 13.

In accordance with possible embodiments, the second mantle 15 may comprise a plurality and of first zones 17 and a plurality of second zones 19 arranged alternately along a circumference of the second mantle 15.

The combination of the rotation of the rollers 12 and 13 in opposite directions with the alternating of zones with protruding patterns and zones without protruding patterns allows compensation of any web 11 drift effects generated due to twisting of the latter on the protruding patterns.

That aspect allows perforated patterns 20 to be made which are spaced apart by a step which may even be close so as to reduce the distance between the outlines of absorbent articles being made and therefore consequently so as to increase the number of articles produced from the same extension of web 11.

According to possible embodiments, the step between the perforated patterns 20 may be determined by a functional relationship having parameters selected in a group constituted by: advancing velocity V of the web 11, difference between the first velocity V1 of the first roller 12 and the second velocity V2 of the second roller 13, extension of the second zone 19 along a circumference of the second mantle 15, and combinations thereof.

According to possible embodiments, the circumference of the second mantle 15 along which the at least a first zone 17 and the at least a second 19 alternate has a portion tangent to the advancement direction of the web 11 between the two rollers 12 and 13.

According to possible embodiments, the extension of the perforated patterns 20 along the advancement direction of the web 11 may be modulated by setting the rotating velocities V1 and V2 of the rollers 12 and 13 and the advancing velocity V of the web 11.

According to possible embodiments, the perforated patterns 20 comprise a plurality of holes. For example, the holes are sized and arranged in relation to the geometry of the protruding patterns 16 and 18.

According to possible embodiments, the first protruding pattern 16 may have a protruding profile inclined by an angle of inclination with respect to the first axis of rotation R1 equal to or less than 90°.

That aspect allows the first protruding pattern 16 to engage the second protruding pattern 18 with an inclination such that it guarantees perforation of the web 11.

In accordance with possible embodiments, the second protruding pattern 18 may have a protruding profile inclined by an angle of inclination with respect to the second axis of rotation R2 equal to or less than 90°.

Thanks to the combined effect of the inclination of the first protruding pattern 16 and of the second protruding pattern 18, at the moment of engagement with the web 11 they are incident on each other and make the holes in correspondence with the intersection of the inclined protruding patterns.

That allows the holes to be located in the desired zones in relation to the intersecting zones and for them to be sized based on the mutual inclination of the two inclined protruding patterns.

According to possible embodiments, the second mantle 15 may have one or more first zones 17 with second protruding patterns 18 having protruding profiles inclined by an angle of inclination with respect to the second axis of rotation R2 which are different from the other first zones 17.

For example, the first zones 17 may have second protruding patterns 18 having protruding profiles inclined by angles of inclination with respect to the second axis of rotation R2 which are opposite in an alternating way, that is to say, one first zone 17 has a second protruding pattern 18 with a first inclination and the next first zone 17 has a second protruding pattern 18 with a second inclination, opposite to the first inclination.

According to possible embodiments, the first protruding pattern 16 and the second protruding pattern 18 may have the same protruding profile inclined so that, in use, the respective inclined protruding profiles of the first protruding pattern 16 and of the second protruding pattern 18 intersect each other in localized zones of the web 11 to locally perforate it.

That aspect guarantees high efficiency and precision in making the perforated patterns 20 which have their holes spaced apart in a uniform way and with a single shape.

Figure 3:
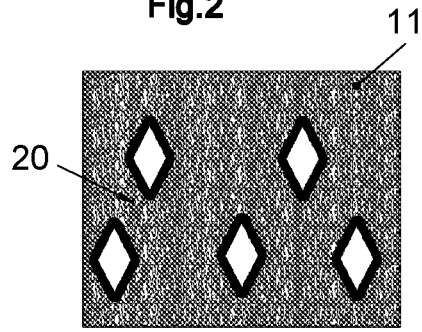
FIG. 3 schematically illustrates a portion of a web provided with holes made by means of a possible embodiment of the present invention.
Figure 4:
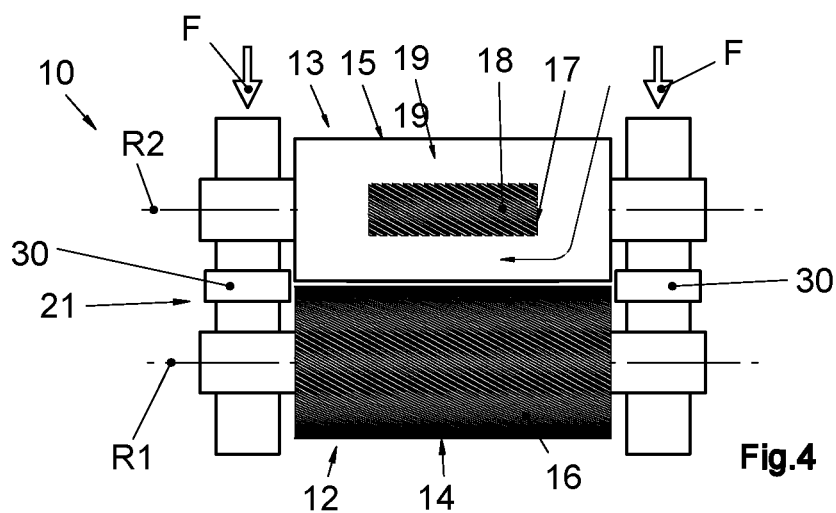
FIG. 4 schematically illustrates a perforating device of an apparatus for producing sanitary absorbent articles according to a possible embodiment of the present invention.
Figure 5:
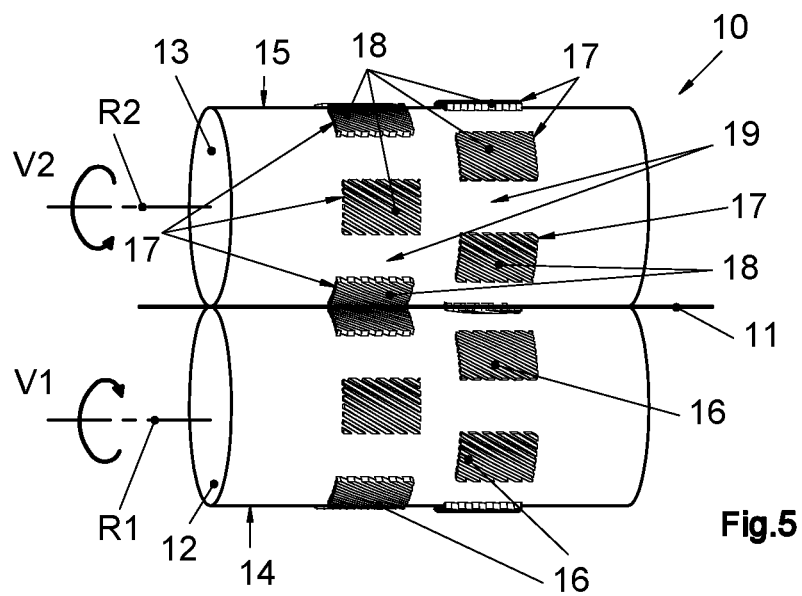
FIG. 5 schematically illustrates a perforating device of an apparatus for producing sanitary absorbent articles according to a possible embodiment of the present invention.
Figure 6:
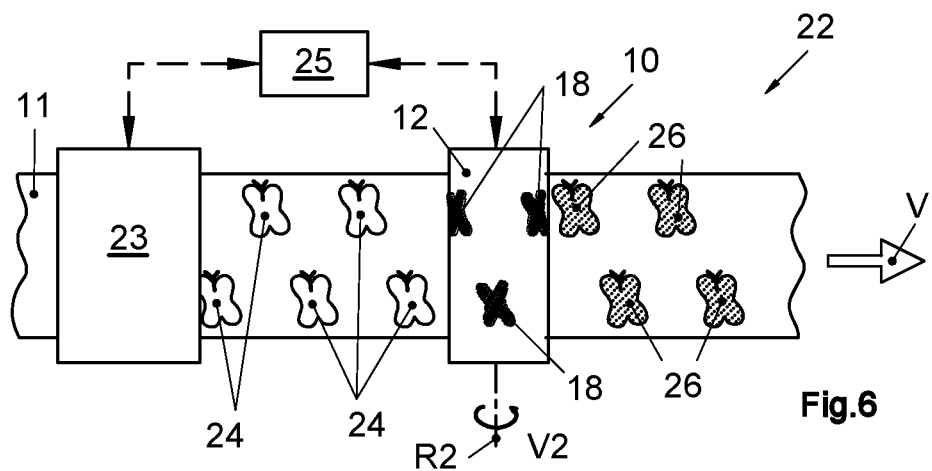
FIG. 6 schematically illustrates a production apparatus according to a possible embodiment of the present invention.
Figure 7:
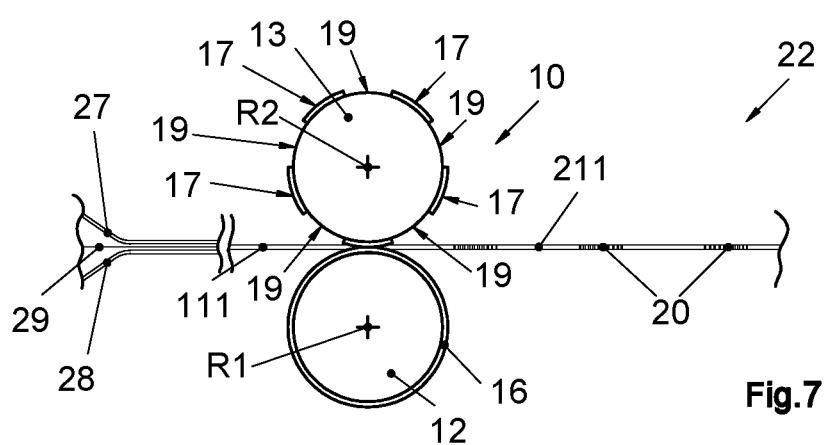
FIG. 7 schematically illustrates a production apparatus according to a possible embodiment of the present invention.

For example, FIG. 3 illustrates a portion of web 11 on which there is a perforated pattern 20 provided with homogeneously distributed holes.

That perforated pattern 20 may be obtained using protruding patterns 16 and 18 which intersect each other locally on the web 11 without interpenetrating each other, that is to say, each having a protruding profile inclined in relation to the respective axis of rotation R1 and R2 to form and "X" shape at the moment of engagement.

In accordance with possible embodiments, the maximum distance between the second axis of rotation R2 and the second zone 19 may be less than the maximum distance between the second axis of rotation R2 and the first zone 17.

That aspect allows contact of the mantles 14 and 15 of the rollers 12 and 13 with the web 11 to be contained while it passes through them. That reduces the possibilities of web 11 snags between the two rollers 12 and 13, as well as unwanted crushing and/or lacerations of the web 11.

According to possible embodiments, the perforating device 10 may comprise at least one spacer member 21 coupled with the first roller 12 and/or with the second roller 13 and configured, in use, to keep the first protruding pattern 16 spaced apart from the surface of the second zone 19 of the second mantle 15 by a distance equal to the distance between the surface of the second zone 19 of the second mantle 15 and the outermost end of the second protruding pattern 18.

According to possible embodiments, the spacer member 21 may be configured, in use, to keep the first protruding pattern 16 spaced apart from the surface of the second zone 19 of the second mantle 15 by a distance equal to the distance between the surface of the second zone 19 of the second mantle 15 and the outermost end of the second protruding pattern 18.

That outermost end corresponds to the most protruding point of the second protruding pattern 18.

In other words, the surface of the second zone 19 being closer to the axis of rotation R2 with respect to the protruding surface of the first zone 17, and keeping the distance between the first protruding pattern 16 and the surface of the second zone 19 equal to the difference between the protruding surface of the first zone 17 and the surface of the second zone 19, the first mantle 14, in use, remains spaced apart from the second mantle 15 in correspondence with the second zones 19 and the first mantle 14 and the second mantle 15 engage with the web 11 in correspondence with the first zones 17.

That aspect allows zeroing of any accidental impacts of the mantles 14 and 15 with the web 11 which could damage it, simultaneously guaranteeing high efficiency and stability of the perforating process, as well as durability of the rollers 12 and 13.

According to possible embodiments, the spacer member 21 may comprise a pair of spacer elements 30 arranged between the axes of rotation R1 and R2 of the rollers 12 and 13 on opposite sides.

According to possible embodiments, those spacer elements 30 are configured to space apart the axes of rotation of the rollers 12 and 13.

The combined action of the forces F applied and of the spacer elements 30 allows definition both of the pressure between the protruding patterns 16 and 18, and of the distance between the rollers 12 and 13 in the portions of the rollers 12 and 13 which do not engage with each other and which allow the web 11 to pass without being perforated, so as to make perforated patterns 20 spaced apart along the extension of the web 11 itself.

In accordance with possible embodiments, the perimeter of the first zone 17 may be shaped in relation to the perimeter of the perforated pattern 20 to be made on the web 11.

That aspect allows determination of the desired shape of the perforated pattern 20 on the web 11 in relation to the shape of the first zones 17. Actually, once the velocities have been set the perforated pattern 20 is intermittently reproduced on the web 11 with perimetric profiles corresponding to the characteristics of the first zones 17.

For example, the perimeter of the first zone 17 may define an area that is circular, elliptical, polygonal, or other.

In relation to the area defined by the perimeter of the first zone 17 and to other operating parameters of the perforating device 10, for example the rotating velocities V1 and V2 of the rollers 12 and 13 and/or the advancing velocity V of the web 11, it is possible to define the zones affected by the perforated patterns 20.

According to possible embodiments, the present invention also relates to an apparatus 22 for producing sanitary absorbent articles comprising at least one perforating device 10 of at least one web 11 according to any of the possible embodiments.

In accordance with possible embodiments, the production apparatus 22 may, if necessary, have dedicated processing units for performing processing on perforated webs 11 downstream of the perforating device 10. For example, it may be provided with an embossing unit placed downstream of the perforating device 10 for making a perforated web 11 provided with embossing.

That simplifies the processing units placed upstream of the perforating device 10 which require a design for non-perforated webs 11 which typically requires less complex processing units. Any modifications to be made to the apparatus and/or the designs of the apparatus which are dedicated to the type of holes made on the web 11 are kept to the processing units placed downstream of the perforating device 10.

In that way, the production apparatus 22 is much more flexible since it adapts to a greater number of types of webs 11 and allows various and different perforated patterns 20 to be made in relation to the production requirements.

In accordance with possible embodiments, the production apparatus 22 may comprise a printing unit 23 placed upstream of the perforating device 10 and configured to print a plurality of graphic patterns 24 spaced apart on the web 11.

According to possible embodiments, the perforating device 10 is configured to make holes in correspondence with the graphic patterns 24 so as to make a plurality of graphic patterns 24 provided with holes spaced apart on the web 11.

That aspect allows elimination of contamination and/or damage to parts of the production apparatus 22 due to the use of printing units on already perforated webs 11, since the ink and/or the laser used for the printing is used on the web 11 before it is perforated.

That eliminates one of the main problems of the prior art which to this day are solved by means of ink containment tanks and/or protective screens which, as well as complicating the layout of the printing unit, necessitate frequent maintenance.

According to possible embodiments, the production apparatus 22 may comprise a management and control unit 25 configured to manage and control the operation of the printing unit 23 and of the perforating device 10 in a coordinated way for making perforated patterns 20 in correspondence with the graphic patterns 24.

According to possible embodiments, the holes of the perforated patterns 20 may be made on the graphic patterns 24, or near the latter without perforating the printed parts of the web 11.

According to possible embodiments, the management and control unit 25 may be functionally coupled with one or more sensors suitable for detecting the operating conditions of the web 11, of the printing unit 23 and of the perforating device 10.

In accordance with possible embodiments, the present invention also relates to a process for perforating at least one web 11 intended for making sanitary absorbent articles.

According to possible embodiments, the perforating process may provide to:

supply the web 11 along an advancement direction at an advancing velocity V;

pass the web 11 between a first roller 12 and a second roller 13 respectively provided with a first mantle 14 and a second mantle 15, wherein the first roller 12 and the second roller 13 rotate in opposite directions respectively around a first axis of rotation R1 at a first velocity V1 and around a second axis of rotation R2, parallel to the first axis of rotation R1, at a second velocity V2 different from the first velocity V1, wherein the first mantle 14 comprises a first protruding pattern 16 and the second mantle 15 comprises at least a first zone 17, wherein a second protruding pattern 18 is present, and at least a second zone 19 without protruding patterns and adjacent to the first zone 17 along a circumference of the second mantle 15;

perforating the web 11 in correspondence with the engagement zones of the first protruding pattern 16 and the second protruding pattern 18 so as to make a plurality of perforated patterns 20 spaced apart along the extension of the web 11.

The perforating process allows the making of intermittent, that is to say, in phase, perforated patterns 20 on a web 11 with high efficiency and precision which allows the requirements of the sector for the production of sanitary absorbent articles to be met.

In accordance with possible embodiments, the perforating process may provide that the advancing velocity V is comprised between the first velocity V1 and the second velocity V2.

That aspect is advantageous since it allows minimizing, if not zeroing, of the drift effects correlated with sequential engagement of the web 11 with the protruding patterns 16 and 18.

The rollers 12 and 13 rotating in opposite directions and the web 11 advancing with advancing velocity V comprised between the velocities V1 and V2 of the two rollers 12 and 13, mean that the drift effect of the web 11 due to each roller 12 and 13 is compensated, rendering the perforating process stable.

According to possible embodiments, the first velocity V1 may be less than the second velocity V2.

In accordance with possible embodiments, the advancing velocity V of the web 11 may be less than or equal to 600 metres/minute.

In accordance with possible embodiments, the ratio between the first velocity V1 and the second velocity V2 may be less than or equal to 0.7.

According to possible embodiments, the ratio between the first velocity V1 and the second velocity V2 may be less than or equal to 0.05.

According to possible embodiments, the ratio between the first velocity V1 and the second velocity V2 may be less than or equal to 0.005.

To guarantee that the perforated patterns 20 are spaced apart by steps consistent with those typical of the sector for the production of sanitary absorbent articles, the diameter of the second roller 13 may be less than or equal to 500 mm.

Those dimensions define the categories of rollers 12 and 13 usable in the sector for the production of sanitary absorbent articles, simultaneously distinguishing them from other types of calendars typical of the rolling of webs 11 which cannot be used for making perforated webs 11 as described in the present invention.

According to possible embodiments, the perforating process may provide that the advancing velocity V is equal to the first velocity V1 or to the second velocity V2.

That aspect allows the velocity V1 or V2 of one of the rollers 12 or 13 to be set with the advancing velocity V of the web 11, so as to be able to determine the shape and spacing of the perforated patterns 20 by setting the velocity V2 or V1 of the other roller 13 or 12.

In accordance with possible embodiments, the perforating process may provide that the first protruding pattern 16 and the second protruding pattern 18 have a protruding profile inclined at the same angle of inclination with respect to the corresponding axis of rotation R1 and R2, wherein the process may provide to perforate the web 11 in correspondence with the intersections of the inclined protruding profiles of the first protruding pattern 16 and of the second protruding pattern 18.

That aspect allows the making of perforated patterns 20 having holes which are localized and distributed uniformly and in a precise and accurate way.

According to possible embodiments, the perforating process may provide that the second zone 19 does not touch the web 11 while the latter passes between the first roller 12 and the second roller 13.

That aspect allows the making of perforated patterns 10 on the web 11 while minimizing the contact of the latter with the rollers 12 and 13 and therefore the likelihood that unwanted snags occur.

In accordance with possible embodiments, the perforating process may provide to print a plurality of graphic patterns 24 spaced apart on the web 11 before making the perforated patterns 20.

That has the advantage of not contaminating and/or damaging parts of the apparatus with ink and/or laser, since the latter are used on a web 11 not yet perforated.

According to possible embodiments, the perforating process may provide to make the perforated patterns 20 in correspondence with the graphic patterns 24.

That aspect allows the combination of graphic patterns 24 with perforated patterns 20 in phase with each other, so as to make perforated graphic patterns 26 having the holes localized inside the printed areas, or even around them.

The possibility of making perforated patterns 20 on graphic patterns 24 in phase allows the making of sanitary absorbent articles having perforated graphic patterns 26 which are homogeneous and without misalignment between them.

In accordance with possible embodiments, the perforating process may provide to make a plurality of embossing on the web 11 after having made the perforated patterns 20.

That allows the apparatus to be fed with a non-perforated web 11 and the making of a web 11 with embossing and having perforated patterns 20 spaced apart along the extension of the web 11.

According to possible embodiments, the perforating process may provide that the web 11 is a composite web 111 comprising a first layer 27, a second layer 28 and at least one elastic element 29 placed between the first layer 27 and the second layer 28.

According to possible embodiments, the first layer 27 and the second layer 28 may comprise a non-woven fabric. For example, the first layer 27 may comprise a first non-woven fabric and the second layer 28 may comprise a second non-woven fabric.

In accordance with possible embodiments, the first non-woven fabric and the second non-woven fabric may be different in relation to the function for which they are intend for the sanitary absorbent article.

According to possible embodiments, the elastic element 29 may comprise an elastic thread, an elastic band, an elastic layer, and combinations thereof.

That aspect allows the combination of the perforation of one or both of the layers 27 and/or 28 of the composite web 111 with the possibility of locally welding them together. Actually, in relation to the velocities V1, V2 and V, to the type of composite web 111 used, to the protruding patterns 16 and 18, and to other parameters such as the temperature or the pressure applied between the rollers 12 and 13, embodiments of the present invention allow the making of perforated composite webs 211 which are locally welded and having perforated patterns 20 which are intermittent, that is to say, made in phase along the extension of the composite web 111.

In accordance with possible embodiments, the perforating process may provide to locally weld the first layer 27 and the second layer 28 together while the elastic element 29 is tensioned. That aspect allows the making of holes and welds with a pattern such that it allows local trapping of the tensioned elastic element 29 so as to be able to obtain a composite web 111 which is gathered in the home position and with perforated patterns 20 spaced apart along the extension of the web 11.

It is clear that the perforating device 10, the production apparatus 22 and the perforating process described above may be subject to modifications and/or additions of parts, without thereby departing from the scope of the present invention. It also remains clear that the first roller 12 and the second roller 13 have been described, for expository purposes only and without limiting the scope of the invention, in relation to the possible embodiment illustrated in the drawings. It is also clear that the characteristics regarding the first roller 12 and the second roller 13 may be applied to inverted parts without thereby departing from the scope of the present invention. The considerations and the embodiments described herein for the first roller 12 may be valid for the second roller 13, and vice versa without thereby departing from the scope of the present invention.

It is also clear that, although the present invention has been described with reference to some specific examples, a person skilled in the art will certainly be able to make many other equivalent embodiments of the perforating device 10, of the production apparatus 22 and of the perforating process having the characteristics expressed in the claims and therefore all covered by the scope of protection that they define.

In the claims below, references in brackets are intended only to facilitate reading and must not be considered to be limiting factors as regards the scope of protection of the specific claims.

The invention claimed is:

1. An apparatus for producing sanitary absorbent articles, comprising:

at least one perforating device of at least one web intended for making said sanitary absorbent articles, wherein said perforating device comprises a first roller and a second roller respectively provided with a first mantle and a second mantle and between which, in use, passes said web, wherein said first roller and said second roller are configured to rotate in opposite directions respectively around a first axis of rotation at a first velocity and around a second axis of rotation, parallel to said first axis of rotation, at a second velocity different from said first velocity, wherein said first mantle comprises a first protruding pattern including a plurality of first protrusions having outermost first end surfaces, and said second mantle comprises at least a first zone, wherein a second protruding pattern is present including a plurality of second protrusions having outermost second end surfaces, and at least a second zone without protruding patterns and adjacent to said first zone along a circumference of said second mantle, wherein said second end surfaces of said of second protruding pattern are configured, in use, to temporally engage said web by engagement with the first end surfaces of said first protruding pattern without interpenetrating the latter for locally perforating said web.

2. The apparatus of claim 1, wherein said second mantle comprises a plurality of said first zones and a plurality of said second zones arranged alternately along a circumference of said second mantle.

3. The apparatus of claim 1, wherein said first protruding pattern has a protruding profile inclined by an angle of inclination with respect to said first axis of rotation equal to or less than 90°.

4. The apparatus of claim 3, wherein said second protruding pattern has a protruding profile inclined by an angle of inclination with respect to said second axis of rotation equal to or less than 90°.

5. The apparatus of claim 4, wherein said first protruding pattern and said second protruding pattern have the same protruding profile inclined so that, in use, the respective inclined protruding profiles of said first protruding pattern and of said second protruding pattern intersect each other in localized zones of said web to locally perforate it.

6. The apparatus of claim 1, wherein a maximum distance between said second axis of rotation and said second zone is less than a maximum distance between said second axis of rotation and said first zone.

7. The apparatus of claim 1, wherein said perforating device comprises at least one spacer member coupled with said first roller and/or with said second roller and configured, in use, to keep said first protruding pattern spaced apart from a surface of said second zone of said second mantle by a distance equal to a distance between the surface of said second zone of said second mantle and an outermost end of said second protruding pattern.

8. The apparatus of claim 1, wherein a perimeter of said first zone is shaped in relation to a perimeter of a perforated pattern to be made on said web.

9. The apparatus of claim 1, further comprising a printing unit placed upstream of said perforating device and configured to print a plurality of graphic patterns spaced apart along an extension of said web, wherein said perforating device is configured to make perforations in correspondence with said graphic patterns so as to make a plurality of perforated graphic patterns spaced apart along the extension of said web.

10. The apparatus of claim 1, wherein said first roller and/or said second roller are coupled with heating means configured to heat said first roller and/or said second roller for perforating, in use, said web by heating it locally.

11. The apparatus of claim 1, wherein engagement of the first and second end surfaces with the at least one web therebetween results in holes being created thereby locally perforating said at least one web.

12. A process for perforating at least one web intended for making sanitary absorbent articles implemented in an apparatus for producing sanitary absorbent articles comprising at least one perforating device as claimed in claim 1, wherein said process comprises:
supplying said web along an advancement direction at an advancing velocity;
passing said web between a first roller and a second roller respectively provided with a first mantle and a second mantle,
wherein said first roller and said second roller rotate in opposite directions respectively around a first axis of rotation at a first velocity and around a second axis of rotation, parallel to said first axis of rotation, at a second velocity different from said first velocity,
wherein said first mantle comprises a first protruding pattern including a plurality of first protrusions having outermost first end surfaces, and said second mantle comprises at least a first zone,
wherein a second protruding pattern is present including a plurality of second protrusions having outermost second end surfaces, and at least a second zone without protruding patterns and adjacent to said first zone along a circumference of said second mantle;
perforating said web in correspondence with the first and second zones of said first protruding pattern and said second protruding pattern by engagement of said first end surfaces with said second end surfaces so as to make a plurality of perforated patterns spaced apart along an extension of said web.

13. The process of claim 12, wherein said advancing velocity is comprised between said first velocity and said second velocity.

14. The process of claim 12, further comprising printing a plurality of graphic patterns spaced apart on said web before making said plurality of perforated patterns.

15. The process of claim 14, further comprising making said plurality of perforated patterns in correspondence with said graphic patterns.

16. The process of claim 12, wherein said web is a composite web comprising a first layer of non-woven fabric, a second layer of non-woven fabric and at least one elastic element placed between said first layer and said second layer, and wherein said process provides to locally weld said first layer and said second layer together while said elastic element is tensioned.

17. The process of claim 12, wherein engagement of the first and second end surfaces with the at least one web therebetween results in holes being created thereby locally perforating said at least one web.

* * * * *